(12) United States Patent
Gil et al.

(10) Patent No.: US 8,067,441 B2
(45) Date of Patent: Nov. 29, 2011

(54) USE OF COLLISMYCIN AND DERIVATIVES THEREOF AS OXIDATIVE STRESS INHIBITORS

(75) Inventors: Ana Martinez Gil, Madrid (ES); Paola Usan Egea, Alpedrete-Madrid (ES); Miguel Medina Padilla, Madrid (ES); Esther Garcia Palomero, Leganes-Madrid (ES); Julia Perez Baz, Trobajo Del Camino-Leon (ES); Rosa Isabel Fernandez Chimeno, Navatejera-Leon (ES); Antonio Medarde Fernandez, Leon (ES); Librada Maria Canedo Hernandez, Onzonilla-Leon (ES); Francisco Romero Millan, Onzonilla-Leon (ES); Ana Castro Morera, Madrid (ES); Mercedes Alonso Cascon, Madrid (ES); Jorge Sanchez Quesada, Tres Cantos-Madrid (ES)

(73) Assignees: Neuropharma, S.A. (ES); Instituto Biomar, S.A. (ES)

( * ) Notice: Subject to any disclaimer, the term of this patent is extended or adjusted under 35 U.S.C. 154(b) by 212 days.

(21) Appl. No.: 11/996,966

(22) PCT Filed: Jul. 28, 2006

(86) PCT No.: PCT/EP2006/007521
§ 371 (c)(1),
(2), (4) Date: Jun. 24, 2008

(87) PCT Pub. No.: WO2007/017146
PCT Pub. Date: Feb. 15, 2007

(65) Prior Publication Data
US 2008/0275088 A1 Nov. 6, 2008
US 2010/0048635 A2 Feb. 25, 2010

(30) Foreign Application Priority Data
Jul. 29, 2005 (EP) .................................. 05380175

(51) Int. Cl.
*A01N 43/40* (2006.01)
*A61K 31/44* (2006.01)
(52) U.S. Cl. .................................................... 514/334
(58) Field of Classification Search .................. 514/334
See application file for complete search history.

(56) References Cited

FOREIGN PATENT DOCUMENTS

| EP | 0 159 640 A1 | 10/1985 |
|---|---|---|
| JP | 5-078322 | 3/1993 |
| JP | 9-012550 | 1/1997 |
| WO | 0189520 A2 | 11/2001 |

(Continued)

OTHER PUBLICATIONS

Stadler M, Bauch F, Henkel T, Mühlbauer A, Müller H, Spaltmann F, and Weber K, "Antifungal actinomycete metabolites discovered in a differential cell-based screening using a recombinant TOPO1 deletion mutant strain," Archiv der Pharmazie, May 2001, 334(5), 143-147.*

(Continued)

*Primary Examiner* — San-Ming Hui
*Assistant Examiner* — Paul Zarek
(74) *Attorney, Agent, or Firm* — Kenneth H. Sonnenfeld; King & Spalding LLP

(57) ABSTRACT

The present invention relates to the use of Collismycin and derivatives thereof as inhibitors of oxidative stress in cells and their use for the preparation of medicaments for the treatment of oxidative stress-induced diseases or conditions, especially neurodegenerative diseases, such as Alzheimer's Disease and Parkinson's Disease.

12 Claims, 4 Drawing Sheets

FOREIGN PATENT DOCUMENTS

| WO | WO 02/053138 | 7/2002 |
|---|---|---|
| WO | 20070031882 A2 | 3/2007 |
| WO | WO 2007/031832 | 3/2007 |

OTHER PUBLICATIONS

Klegeris A and McGreer PL, "Non-Steroidal Anti-Inflammaotry Drugs (NSAIDs) and Other Anti-Inflammatory Agents in the Treatment of Neurodegenerative Diseas," Current Alzheimer Research, Jul. 2005, 2(3), 355-365.*

Shindo K, Yamagishi Y, Okada Y, and Kawai H, "Collismycins A and B, novel non-steroidal inhibitors of dexamethasone-glucocorticoid receptor binding," Journal of Antibiotics, Sep. 1994, 47(9), 1072-1074.* van De Waterbeemd H, Smith DA, Beaumont K, and Walker DK, "Property-based design: optimization of drug absorption and pharmacokinetics," Journal of Medicinal Chemistry, Apr. 2001,44(9), 1313-1333.*

Vippagunta SR, Brittain HG, and Grant D J, "Crystalline solids," Advanced Drug Delivery Reviews, May 2001,48(1), 3-26.*

Adis R&D Insight, "Collismycin A," Adisinsight Accession No. 1998:4421, Apr. 7, 1995.

Adis R&D Insight, "Collismycin B," Adisinsight Accession No. 1998:4426, Apr. 10, 1995.

Cristalli, G. et al., "2,2'-Bipyridyl-6-carboxamidoximes with potential antitumor and antimicrobial properties," Farmaco, Edizione Scientifica, (1986) vol. 41, Nr:7, pp. 499-507.

Goodman & Gilman's The Pharmacological Basis of Therapeutics, 11th edition, McGraw-Hill Publishers, 2006, p. 673.

Honer et al., "Glucocorticoid Receptor Antagonism by Cyproterone Acetate and RU486," Molecular Pharmacology, (2003) vol. 63, No. 5, pp. 1012-1020.

Miner et al., "A Nonsteroidal Glucocorticoid Receptor Antagonist," Molecular Endocrinology, (2003) vol. 17, No. 1, pp. 117-127.

Park, H.-R., et al., "Regulation of grp78 transcription by substances of microbial origin," Society for Neuroscience Abstracts, (2001) vol. 27, No. 1, pp. 1486.

Park, H.-R. et al., "Versipelostatin, a novel GRP78/Bip molecular chaperone down-regulator of microbial origin," Tetrahedron Letters, (2002) vol. 43, Nr:39, pp. 6941-6945.

Reines et al., "Rofecoxib, No effect on Alzheimer's disease in a 1-year, randomized, blinded, controlled study," Neurology, (Jan. 2004), vol. 62, pp. 66-71.

Rosen et al., "The Search for Safer Glucocorticoid Receptor Ligands," Endocrine Reviews, (Published online Apr. 6, 2005), vol. 26, No. 3, pp. 452-464.

Tsuge, N. et al., "Novel antibiotics pyrisulfoxin A and B produced by *Streptomyces californicus*," Journal of Antibiotics, (1999) vol. 52, Nr:5, pp. 505-507.

van Goal, W.A. et al., "Anti-inflammatory therapy in Alzheimer's disease: is hope still alive?" J. Neurol., (2003) vol. 250, pp. 788-792.

Adler et al., "Vitamin E treatment of tardive dyskinesia," 1993, 50: pp. 1405-1407, Abstract only, Am J Psychiatry.

Alexandrova et al., "Oxidative Stress During the Chronic Phase After Stroke," 2005, 1:39(3), pp. 297-316, Free Radical Biology & Medicine.

Allard et al., "Effects of vitamin E and C supplementation on oxidative stress and viral load in HIV infected subjects," Journal, Sep. 10, 1998, 12: pp. 1653-1659, Abstract only, AIDS.

Asimakis et al., "Postischemic Recovery of Contractile Function is Impaired in SOD2+/− but Not SOD1 +/− Mouse Hearts," 2002, 105, pp. 981-986, Circulation.

Babcock et al., "Regulation of Mitochondrial Iron Accumulation by Yfh1p, a Putative Homolog of Frataxin," Jun. 13, 1997, pp. 1709-1712, vol. 276, No. 5319, Science, Abstract only.

Barnes et al., "Nuclear Factor kB-A Pivotal Transcription Factor in Chronic Inflammatory Diseases", Apr. 10, 1997, 336: pp. 1066-1071, The New England Journal of Medicine.

Baum et al., "HIV-1 infection in women is associated with severe nutritional deficiencies,", Dec. 1, 1997, vol. 16, pp. 272-278, J Acquir Immune Defic Syndr Hum Retrovirol, Abstract only.

Beal et al., "Increased 3-Nitrotyrosine in Both Sporadic and Familial Amyotrophic Lateral Sclerosis," Oct. 1997, pp. 644-654, vol. 42, Issue 4, Annals of Neurology, Abstract only.

Beal et al., "3-Nitropropionic Acid Neurotoxicity Is Attenuated in Copper/Zinc Superoxide Dismutase Transgenic Mice," 1995, pp. 919-922, vol. 65, Issue 2, Journal of Neurochemistry, Abstract only.

Bjugstad et al., "Preventive actions of a synthetic antioxidant in a novel animal model of AIDS dementia," Jun. 8, 1998, pp. 349-357, 795, Brain Res., Abstract only.

Bo et al., "Induction of Nitric Oxide Synthase in Demyelinating Regions of Multiple Sclerosis Brains," Nov. 1994, pp. 778-786, vol. 36, Issue 5, Annals of Neurology, Abstract only.

Bolaños et al., "Effect of Peroxynitrite on the Mitochondrial Respiratory Chain: Differential Susceptibility of Neurones and Astrocytes in Primary Culture," 1995, pp. 1965-1972, vol. 64, Issue 5, Journal of Neurochemistry, Abstract only.

Boven et al., "Increased Peroxynitrite Activity in AIDS Dementia Complex: Implications for the Neuropathogenesis of HIV-1 Infection," 1999, pp. 4319-4327, 162 (7), J. Immunol., The American Association of Immunologists.

Brodsky et al., "Hyperglycemic switch from mitochondrial nitric oxide to superoxide production in endothelial cells," 2002, pp. H2130-H2139, 283, American Journal Physiol Heart Circ Physiol.

Brown et al., "Amyotrophic Lateral Sclerosis: Recent Insights from Genetics and Transgenic Mice," Mar. 10, 1995, pp. 687-692, vol. 80, Cell.

Brown et al., "Vitamin E, Lipids, and Lipid Peroxidation Products in Tardive Dyskinesia," Jun. 15, 1998, pp. 863-867, vol. 43, Issue 12, Biological Psychiatry, Abstract only.

Browne et al., "Oxidative Damage and Metabolic Dysfunction in Huntington's Disease: Selective Vulnerability of the Basal Ganglia," May 1997, pp. 646-653, vol. 41, Issue 5, Annals of Neurology, Abstract only.

Browne et al., "Oxidative Stress in Huntington's Disease," Jan. 1999, pp. 147-163, 9 (1), Brain Pathology.

Bruijn, et al., "Elevated Free Nitrotyrosine Levels, but not Protein-bound Nitrotyrosine or Hydroxyl Radicals, Throughout Amyotrophic Lateral Sclerosis (ALS)-like Disease Implicate Tyrosine Nitration as an Aberrant in vivo Property of one Familial ALS-linked Superoxide Dismutase 1 Mutant," Jul. 1997, pp. 7606-7611, vol. 94, Proc. Natl Acad. Sci. USA.

Butterworth et al., "Trinucleotide (CAG) repeat length is positively correlated with the degree of DNA fragmentation in Huntington's disease striatum," Jun. 30, 1998, pp. 49-53. vol. 87, Issue 1, Neuroscience, Abstract only.

Buttke et al., "Oxidative stress as a mediator of apoptosis," Jan. 1994, pp. 7-10, vol. 15 (1), Immunol Today, Abstract only.

Buyse et al., "Idebenone treatment in Friedreich's ataxia Neurological, cardiac, and biochemical monitoring," 2003, pp. 1679-1681, vol. 60, Neurology, Abstract only.

Calabrese et al., Oxidative stress, mitochondrial dysfunction and cellular stress response in Friedreich's ataxia, 2005, pp. 145-162, vol. 233, Issue 1-2, Journal of Neurological Sciences.

Carri et al., "Neurodegeneration in Amyotrophic Lateral Sclerosis: the Role of Oxidative Stress and Altered Homeostasis of Metals," 2003, pp. 365-374, vol. 61, Brain Research Bullentin.

Ceriello et al., "Detection of Nitrotyrosine in the Diabetic Plasma: Evidence of Oxidative Stress," 2001, pp. 834-838, vol. 44, Diabetologia.

Chen et al., "Extracellular Superoxide Dismutase Transgene Overexpression Preserves Postischemic Myocardial Function in Isolated Murine Hearts," 1996, pp. 412-417, vol. 94(9), Circulation, Abstract only.

Cirelli et al., "Serum selenium concentration and disease progress in patients with HIV infection," Apr. 1991, pp. 211-214, vol. 24, Issue 2, Clin Biochem., Abstract only.

Clausen et al., "Selenium in chronic neurologic diseases. Multiple sclerosis and Batten's disease.," Jan.-Apr. 1988, pp. 179-203, vol. 15, Biol Trace Elem Res., Abstract only.

Cooper, "Multiple sclerosis: an immune legacy?," Oct. 1997, pp. 307-311. vol. 49. Issue 4. Med Hypotheses. Abstract only.

Costello et al., "Oxidative injury in epilepsy potential for antioxidant therapy," 2004, pp. 541-553, vol. 4(3), Expert. Rev. Neurotherapeutics.

Dakhale et al., "Oxidative Damage and Schizophrenia: The Potential Benefit by Atypical Antipsychotics," 2004, pp. 205-209, vol. 49, Issue 4, Neuropsychobiology, Abstract only.

De La Monte et al., "Oxidative stress and hypoxia-like injury cause Alzheimer-type molecular abnormalities in central nervous system neurons," Sep. 2000, pp. 1471-1481, vol. 57, Cell Mol Life Sci., Abstract only.

Delmas-Beauvieux et al., "The enzymatic antioxidant system in blood and glutathione status in human immunodeficiency virus (HIV)-infected patients: effects of supplementation with selenium or β-Carotene[1,2]," 1996, pp. 101-107, vol. 64, Am J Clin Nutr.

De Micheli et al., "Ischemia-Reperfusion Myocardial Injury," Oct.-Dec. 2003, vol. 73(4), pp. 284-290, Arch. Cardiol. Mex., Abstract only.

Devi et al., "Cocaine-induced peroxidative stress in rat liver: antioxidant enzymes and mitochondria", 1996, pp. 359-366, vol. 1, J. Pharmacol Exp Ther., Abstract only.

Driggers et al., "Mapping frequencies of endogenous oxidative damage and the kinetic response to oxidative stress in a region of rat mtDNA", 1997, pp. 4362-4369, vol. 25, No. 21, Nucleic Acids Res.

Durany et al., "Investigations on oxidative stress and therapeutical implications in dementia," 1999, pp. 68-73, vol. 249 (Suppl 3), Eur Arch Psychiatry Clin Neurosci., Abstract only.

Egan et al., "Treatment of Tardive Dyskinesia with Vitamin E," 1992, pp. 773-777, vol. 149, Am. J. Psychiatry, Abstract only.

Elkashef et al., "Vitamin E in the Treatment of Tardive Dyskinesia," 1990, pp. 505-506, vol. 147, Am. J. Psychiatry, Abstract only.

El Kossi, et al., "Oxidative Stress in the Context of Acute Cerebrovascular Stroke," 2000, pp. 1889-1892, vol. 31, Stroke.

Favier et al., "Antioxidant Status and Lipid Peroxidation in Patients Infected with HIV," Jun. 1994, pp. 165-180, vol. 91, Chemico-Biological Interactions, Abstract only.

Ferrante, et al., "Evidence of Increased Oxidative Damage in Both Sporadic and Familial Amyotrophic Lateral Sclerosis," 1997, pp. 2064-2074, vol. 69, J. Neurochem.

Foury et al., "Deletion of the yeast homologue of the human gene association with Fredreich's ataxia elicits iron accumulation in mitochondria," 1997, pp. 373-377, vol. 411, FEBS Letter.

Fujimura et al., "Neuroprotective effect of an Antioxidant in Ischemic Brain Injury Involvement of Neuronal Apoptosis," 2005, pp. 59-66, vol. 2, No. 1, Neurocrit Care, Abstract only.

Gilgun-Sherki et al., "Antioxidant Therapy in Acute Central Nervous System Injury: Current State," Jun. 2002, pp. 271-284, vol. 54, No. 2, Pharmacological Reviews.

Gilgun-Sherki et al., "The role of oxidative stress in the pathogenesis of multiple sclerosis:The need for effective antioxidant therapy," 2004, pp. 261-268, vol. 251 (3), J. Neurol.

Giordano, "Oxygen, oxidative stress, hypoxia, and heart failure," Mar. 2005, pp. 500-508, vol. 115, No. 3, The Journal of Clinical Investigation.

Goebel et al, "Juvenile Huntington chorea: Clinical, ultrastructural, and biochemical studies," 1978, pp. 23-31, vol. 28, Neurology, Abstract only.

Gray et al.,"Neuronal apoptosis in human immunodeficiency virus infection," May 2000, pp. S38-43, vol. 6, Suppl 1, J. Neurovirol., Abstract only.

Greene et al., "Caloric Restriction Inhibits Seizure Susceptibility in Epileptic EL Mice by Reducing Blood Glucose," 2001, pp. 1371-1378, vol. 42(11), Epilepsia.

Gupta et al., "Prevention of Kainic Acid Seizures-Induced Changes in Levels of Nitric Oxide and High-Energy Phosphates by 7-Nitroindazole in Rat Brain Regions," Aug. 15, 2003, pp. 184-192, vol. 981, Issue 1-2, Brain Research, Abstract only.

Guzik et al., "Vascular Superoxide Production by NAD(P)H Oxidase: Association with Endothelial Dysfunction and Clinical Risk Factors," 2000, pp. e85-e90, vol. 86, Circulation Research.

Guzik et al., "Mechanisms of Increased Vascular Superoxide Production in Human Diabetes Mellitus: Role of NAD(P)H Oxidase and Endothelial Nitric Oxide Synthase," 2002, pp. 1656-1662, vol. 105, Circulation.

Hall, "Novel inhibitors of iron-dependent lipid peroxidation for neurodegenerative disorders, " 1992, pp. S137-S142, vol. 32, Ann Neurol., Abstract only.

Hansen et al., "Suppression of hyperacute and passively transferred experimental autoimmune encephalomyelitis by the anti-oxidant, butylated hydroxyanisole, " 1994, pp. 69-77, vol. 62, Issue 1, Abstract only, J Neurimmunol.

Hausse et al., Idebenone and reduced cardiac hypertrophy in Friedreich's ataxia, 2002, pp. 346-349, vol. 87, Heart, Abstract only.

Hogg et al, "Nitric oxide and lipid peroxidation," May 5, 1999, pp. 378-384, vol. 1411, Issues 2-3, Biochimica et Biophysica Acta (BBA)-Bioenergetics, Abstract only.

Holtzman et al., "Creatine Increases Survival and Suppresses Seizures in the Hypoxic Immature Rat," Sep. 1998, pp. 410-414, vol. 44, Issue 3, Pediatr. Res.

Holtzman et al., "In Vivo Development of Brain Phosphocreatine in Normal and Creatine-Treated Rabbit Pups", 1999, pp. 2477-2484, vol. 73, Journal of Neurochemistry.

Hutter, "On the causes of multiple sclerosis," Aug. 1993, pp. 93-96, vol. 41, Issue 2, Med Hypotheses, Abstract only.

Inoguchi et al., "High Glucose Level and Free Fatty Acid Stimulate Reactive Oxygen Species Production Through Protein Kinase C—Dependent Activation of NAD(P)H Oxidase in Cultured Vascular Cells," 2000, pp. 1939-1945, vol. 49, Diabetes.

Israël et al., "Oxidative stress in human immunodeficiency virus infection," Dec. 1997, pp. 864-870, vol. 53, Cell Mol Life Sci., Abstract only.

Jersild et al., " Histocompatibility Determinants in Mutiple Sclerosis, with Special Reference to Clinical Course," Dec. 1973, pp. 1221-1225, vol. 302, Issue 7840, The Lancet, Abstract only.

Johansen et al., "Oxidative Stress and the Use of Antioxidants in Diabetes: Linking Basic Science to Clinical Practice," 2005, vol. 4(5), pp. 1-11, Cardiovascular Diabetology.

Kashiwagi et al., "Endothelium-Specific Activation of NAD(P)H Oxidase in Arotas of Exogenously Hyperinsulinemic Rats," 1999, pp. E976-E983, vol. 277, AmJ Physiol Endocrinol Metab.

Khatri et al., "Vascular Oxidant Stress Enhances Progression and Angiogensis of Experimental Atheroma," 2004, pp. 520-525, vol. 109, Circulation.

Kontush et al., "Influence of vitamin E and C supplementation on lipoprotein oxidation in patients with Alzheimer's disease," Aug. 2001, pp. 345-354, vol. 31, Issue 3, Free Radic. Biol. Med., Abstract only.

Kontush et al., "Vitamin E in Neurodegenerative Disorders: Alzheimer's Disease," Dec. 2004, pp. 249-262, vol. 1031, Annals of NY Academy of Sciences, Abstract only.

Koutsilieri et al., "Regulation of glutathione and cell toxicity following exposure to neurotropic substances and human immunodeficiency virus-1 in vitro," 1997, pp. 342-349, vol. 5, J. Neurovirol.

Kulkarni et al., "Pathophysiology and Drug Therapy of Tardive Dyskinesia: Current Concepts and Future Perspectives," 2003, vol. 39(1), Drugs Today.

Kumar et al., Oxidative Stress and Apoptosis in Heart Dysfunction, 2002, pp. 662-668, vol. 27 (7), Herz.

Langemann et al., "Measurement of Low-Molecular-Weight Antioxidants, Uric Acid, Tyrosine, and Tryptophan in Plagues and White Matter from Patients With Multiple Sclerosis," 1992, pp. 248-252, vol. 32(5), Eur. Neurol., Abstract only.

Lehmann et al., "Oral administration of the oxidant-scavenger N-acetyl-L-cysteine inhibits acute experimental autoimmune encephalomyelitis," Feb. 1994, pp. 35-42, vol. 50, , Abstract only, J Neuroimmunol.

Levine, "The role of reactive oxygen species in the pathogenesis of multiple sclerosis," 1992, pp. 271-274, vol. 39, Issue 3, Med Hypotheses, Abstract only.

Liang et al., "Mitochondrial superoxide production in kainate-induced hippocampal damage," Nov. 2000, pp. 563-570, vol. 101, Issue 3, Abstract only, Neuroscience.

Liu et al., "Bilirubin as a potent antioxidant suppresses experimental autoimmune encephalomyelitis: implications for the role of oxidative stress in the development of multiple sclerosis," Jun. 2003, pp. 27-35, vol. 139, Issue 1, MS. Journal of Immunology, Abstract only.

Lohr et al., "Increased indices of free radical activity in the cerebrospinal fluid of patients with tardive dyskinesia," Sep. 1990; pp. 535-539, vol. 28, Biol Psychiatry, Abstract only.

Lovell et al., "Elevated thiobarbituric acid-reactive substances and antioxidant enzyme activity in the brain in Alzheimer's disease," 1995, pp. 1594-1601, vol. 45, Neurology, Abstract only.

Lu et al., Oxidative damage to mitochondrial DNA and activity of mitochondrial enzymes in chronic active lesions of multiple sclerosis,, 2000, pp. 95-103, 2000, vol. 177, Issue 2, J Neurolo Sci., Abstract only.

MacGregor et al., "Ascorbate Attenuates the Systemic Kainate-Induced Neurotoxicity in the Rat Hippocampus," Jul. 15, 1996, pp. 133-144, vol. 727, Issue 1-2, Brain Research, Abstract only.

MacKensen et al., "Neuroprotection from Delayed Postischemic Administration of a Metalloporphyrin Catalytic Antioxidant", Jul. 1, 2001, pp. 4582-4592, vol. 21 (13), J. Neurosci.

Madamanchi et al., "Oxidative Stress and Vascular Disease," 2005, pp. 29-38, vol. 25, Arteriosclerosis, Thrombosis, and Vascular Biology.

Madamanchi et al., "Oxidative Stress in Atherogenesis and Arterial Thrombosis: the Disconnect Between Cellular Studies and Clinical Outcomes" 2005, vol. 3(2), pp. 254-267, Journal of Thrombosis and Haemostasis.

Mahadik et al., "Oxidative Stress and Role of Antioxidant and W-3 Essential Fatty Acid Supplementation in Schizophrenia," 2001, pp. 463-493, vol. 25(3), Prog. Neuropsychopharmacol and Biol Psychiatry.

Malfroy et al., "Prevention and Suppression of Autoimmune Encephalomyelitis by EUK-8, a Synthetic Catalytic Scavenger of Oxygen-Reactive Metabolites," Apr. 10, 1997, pp. 62-68, vol. 177, Issue 1, Cell Immunol., Abstract only.

Marcus et al., "Increased Peroxidation and Reduced Antioxidant Enzyme Activity in Alzheimer's Disease," Mar. 1998, pp. 40-44, vol. 150, Issue 1, Exp. Neurol., Abstract only.

Mariotti et al., "Idebenone treatment in Friedreich patients: One-year-long randomized placebo-controlled trial," 2003, pp. 1676-1679, vol. 60, Neurology, Abstract only.

Marracci et al., "Alpha lipoic acid inhibits T cell migration into the spinal cord and suppresses and treats experimental autoimmune encephalomyelitis," Oct. 2002, pp. 104-114, vol. 131, Issue 1, J. Neuroimmunol., Abstract only.

Matsuyama et al., Cytokines and HIV infection: is AIDS a tumor necrosis factor disease?, 1991, pp. 1405-1417, vol. 5, AIDS, Abstract only.

May et al., "The mechanism of glutamate-induced degeneration of cultured Huntington's disease and control fibroblasts," Aug. 1985, pp. 101-112, vol. 70, Issue 1, Journal of Neurological Sciences, Abstract only.

McCarty, "Insulin's stimulation of endothelial superoxide generation may reflect up-regulation of isoprenyl transferase activity that promotes rac translocation," Jun. 2002, pp. 472-475, vol. 58, Issue 6, Med Hypotheses, Abstract only.

McCreadie et al, "The Nithsdale Schizophrenia Surverys, XIV: Plasma Lipid Peroxide and Serum Vitamin E Levels in Patients with and without Tardive Dyskinesia, and in Normal Subjects," 1995, pp. 610-617, vol. 167, The British Journal of Psychiatry, Abstract only.

Michel et al., "Cu, Zn- and Mn-superoxide dismutase levels in brains of patients with schizophrenic psychosis," 2004, pp. 1191-1201, vol. 111(9), J Neural Transm.

Moreira et al., "Therapeutic potential of oxidant mechanisms in Alzheimer's disease," Nov. 2004, pp. 995-1004, vol. 4, No. 6, Expert Review of Neurotherapeutics, Abstract only.

Moreira et al., "Oxidative Damage and Alzheimer's Disease: Are Antioxidant Therapies Useful?," Jan.-Feb. 2005, pp. 13-19, vol. 18(1), Drug News Perspect.

Moreira et al., "Oxidative Stress and Neurodegeneration," Jun. 2005, pp. 545-552, vol. 1043, Annals of NY Academy of Sciences, Abstract only.

Mori et al., "The Anticonvulsant Zonisamide Scavenges Free Radicals," Apr. 1998, pp. 153-158, vol. 30, Issue 2, Epilepsy Research, Abstract only.

Nishikawa et al. "Normalizing mitochondrial superoxide production blocks three pathways of hyperglycaemic damage," Apr. 13, 2000, pp. 787-790, vol. 404, Letters to Nature, Abstract only.

Nishioka et al., "Evidence for Oxidative DNA Damage in the Hippocampus of Elderly Patients with Chronic Schizophrenia," Mar./Apr. 2004, pp. 167-175, vol. 12, Issue 2, American Journal of Geriatric Psychiatry, Abstract only.

Ohara et al. "Hypercholesterolemia Increases Endothelial Superoxide Anion Production," Jun. 1993, pp. 2546-2551, vol. 91, J Clin Invest.

Olmsted et al., "Selenium supplementation of symptomatic human immunodeficiency virus infected patients," Apr.-May 1989, pp. 59-65, vol. 20, Biol Trace Elem Res., Abstract only.

Pace et al., "The role of oxidative stress in HIV disease ," Oct. 1995, pp. 523-528, vol. 19, Issue 4, Free Radical Biology and Medicine, Abstract only.

Patel, "Mitochondrial Dysfunction and Oxidative Stress: Cause and Consequence of Epileptic Seizures," 2004, pp. 1951-1962, vol. 15;37(12), Free Radic Biol Med.

Pedersen et al., "Protein Modification by the Lipid Peroxidation product 4-Hydroxynonenal in the Spinal Cords of Amyotrophic Lateral Sclerosis Patients," Nov. 1998, pp. 819-824, vol. 44, Issue 5, Annals of Neurology.

Peet et al. "Tardive dyskinesia, lipid peroxidation and sustained amelioration with vitamin E treatment," 1993, pp. 151-153, vol. 8, Int Clin Psychopharmacol., Abstract only.

Pennathuret al., "A hydroxyl radical-like species oxidizes cynomolgus monkey artery wall proteins in early diabetic vascular disease,".Apr. 2001, pp. 853-860, vol. 107, J. Clin. Invest.

Piemonte et al., "Glutathione in Blood of Patients with Friedreich's Ataxia," 2001, pp. 1007-1011, vol. 31, European Journal of Clinical Investigation.

Polidori, et al., "Increased Plasma Levels of Lipid Hydroperoxides in Patients With Ischemic Stroke," Sep. 1998, pp. 561-567, vol. 25, Issues 4-5, Free Radic Biol Med., Abstract only.

Portera-Cailliau et al., "Evidence for Apoptotic Cell Death in Huntington Disease and Excitotoxic Animal Models," May 1995, pp. 3775-3787, vol. 15, The Journal of Neuroscience.

Puccio et al., " Recent advances in the molecuar pathogenesis of Fredreich ataxia", 2000, pp. 887-892, vol. 9, No. 6, Human Molecular Genetics.

Ranjekar etl al., "Decreased antioxidant enzymes and membrane essential polyunsaturated fatty acids in schizophrenic and bipolar mood disorder patients," Dec. 1, 2003, pp. 109-122, vol. 121(2), Psychiatry Res.

Rao et al., "Role of Oxidative Stress and Antioxidants in Neurodegenerative Diseases," Jan. 2002 , pp. 291-309(19), vol. 5, No. 5, Nutritional Neuroscience.

Recchioni et al. "Apoptosis in human aortic endothelial cells induced by hyperglycemic condition involves mitochondrial depolarization and is prevented by N-acetyl-L-cysteine," Nov. 2002, pp. 1384-1388, vol. 51, Issue 11, Metabolism, Abstract only.

Roederer et al., "Cytokine-stimulated human immunodeficiency virus replication is inhibited by N-acetyl-L-cysteine," Jun. 1990, pp. 4884-4888, vol. 87, Proc Natl Acad Sci USA.

Rong et al., "EUK-134, a synthetic superoxide dismutase and catalase mimetic,prevents oxidative stress and attenuates kainateinduced neuropathology," Aug. 1999, pp. 9897-9902, vol. 96, Proc. Natl. Acad. Sci. USA.

Rustin et al., "Effect of idebenone on cardiomyopathy in Friedreich's ataxia: a preliminary study," Aug. 1999, pp. 477-479, vol. 354 , Issue 9177, The Lancet, Abstract only.

Ruuls et al., "Reactive oxygen species are involved in the pathogenesis of experimental allergic encephalomyelitis in Lewis rats," Feb. 1995, pp. 207-217, vol. 56, Issue 2, J Neuroimmunol., Abstract only.

Sacktor et al., "Novel markers of oxidative stress in actively progressive HIV dementia," Dec. 2004, pp. 176-184, vol. 157, Issue 1, Journal of Neuroimmunology, Abstract only.

Sano et al., "A Controlled Trial of Selegiline, Alpha-Tochopherol, or Both as Treatment of Alzheimer's Disease," Aug. 24, 1997, pp. 1216-1222, vol. 336, The New England Journal of Medicine.

Sappey et al., "Stimulation of glutathione peroxidase activity decreases HIV type 1 activation after oxidative stress," Nov. 1994, pp. 1451-1461, vol. 10(11), AIDS Res Hum Retroviruses, Abstract only.

Schrauzer et al., "Selenium in the maintenance and therapy of HIV-infected patients," Jun. 1994, pp. 199-205, vol. 91(2-3), Chemico-Biol Interactions, Abstract only.

Schreck et al., "Reactive oxygen intermediates as apparently widely used messengers in the activation of the NF-ΝB transcription factor and HIV-1," 1991, pp. 2247-2258, vol. 10, No. 8, The EMBO Journal.

Schulz et al., "Involvement of Oxidative Stress in 3-Nitropropionic Acid Neurotoxicity," Aug. 1996, pp. 167-171, vol. 29, Issue 2, Neurochemistry International, Abstract only.

Schulz et al, "Neuroprotective strategies for treatment of lesions produced by mitochondrial toxins: Implications for neurodegenerative diseases," Apr. 1996, pp. 1043-1048, vol. 71, Issue 4, Neuroscience, Abstract only.

Schulz et al., "Glutathione, Oxidative Stress and Neurodegeneration," Eur. J. Biochem., Feb. 2000, pp. 4904-4911, vol. 267.

Schulz et al., "Oxidative stress in patients with Friedreich ataxia," 2000, pp. 1719-1721, vol. 55, Neurology, Abstract only.

Segovia et al., "Oxidative damage in Huntington's Disease," 2004, pp. 321-334, vol. 277, Methods in Molecular Biology.

Shi et al., "Neuronal apoptosis induced by HIV-1 Tat protein and TNF-alpha: potentiation of neurotoxicity mediated by oxidative stress and implications for HIV-1 dementia," Jun. 1998, pp. 281-290, vol. 4, J. Neurovirol., Abstract only.

Shoichet et al., "Frataxin promotes antioxidant defense in a thiol-dependent manner resulting in diminished malignant transformation in vitro," 2002, pp. 815-821, vol. 11, No. 7, Human Molecular Genetics.

Shor-Posner et al., "Neuroprotection in HIV-Positive Drug Users: Implications for Antioxidant Therapy." Oct. 1, 2002, pp. S84-S88, vol. 31, Suppl 2, J Acquir Immune Defic Syndr.

Smith et al., "Presence of 4-Hydroxynonenal in Cerebrospinal Fluid of Patients with Sporadic Amyotrophic Lateral Sclerosis," Oct. 1998, pp. 696-699, vol. 44, Issue 4, Annals of Neurology, Abstract only.

Soccio et al., "Oxidative Stress and Cardiovascular Risk: the Role of Vascular NAD(P)H Oxidase and its Genetic Variants," May 2005, pp. 305-314, vol. 35, Issue 5, European J. Clin. Invest., Abstract only.

Staal et al., "Intracellular thiols regulate activation of nuclear factor κCB and transcription of human immunodeficiency virus," Dec. 1990, pp. 9943-9947, vol. 87, Proc Natl Acad Sci USA.

Stables et al., "Therapy Discovery for Pharmacoresistant Epilepsy and for Disease-Modifying Therapeutics: Summary of the NIH/NINDS/AES Models II Workshop," 2003, pp. 1472-1478, vol. 44(12), Epilepsia.

Sung et al., "Early Vitamin E supplementation in young but not aged mice reduces Aβ levels and amyloid deposition in a transgenic model of Alzheimer's Disease," Dec. 2004, pp. 323-325, vol. 18, FASEB J.

Syburra et al., "Oxidative stress in patients with multiple sclerosis," May-Jun. 1999, pp. 112-115, vol. 71(3), Ukr Biokhim Zh., Abstract only.

Tan et al., "Melatonin protects hippocampal neurons in vivo against kainic acid-induced damage in mice," Nov. 1, 1998, pp. 382-389, vol. 54, Issue 3, Journal of Neuroscience Research, Abstract only.

Tellez-Nagel et al., "Studies on Brain Biopsies of Patients With Huntington's Chorea," 1995, pp. 308-332, vol. 33, Journal of Neuropathol & Experimental Neurology, Abstract only.

Todorova et al., "The Ketogenic Diet Inhibits Epileptogenesis in EL Mice: A Genetic Model for Idiopathic Epilepsy," 2000, pp. 933-940, vol. 41(8), Epilepsia.

Tohgi et al., "Remarkable Increase in Cerebrospinal Fluid 3-Nitrotyrosine in Patients with Sporadic Amyotrophic Lateral Sclerosis," Jul. 1999, pp. 129-131, vol. 46, Issue 1, Annals of Neurology, Abstract only.

Van Der Goes et al., "Reactive oxygen species are required for the phagocytosis of myelin by macrophages," 1998, pp. 67-75, vol. 92, Issue 1, J Neuroimmunol., Abstract only.

Vatassery et al., "High Doses of Vitamin E in the Treatment of Disorders of the Central Nervous System in the Aged[1-3]," 1999, pp. 793-801, vol. 70, Am. J. Clin. Nutr.

Vega-Lopez et al., "Oxidative stress and antioxidant supplementation in the management of diabetic cardiovascular disease," 2004, pp. 24-32, vol. 52, No. 1, J Investig Med., Abstract only.

Vladimirova et al., "Oxidative damage to DNA in plaques of MS brains," 1998, pp. 413-418, vol. 4, Mult Scler., Abstract only.

Vladimirova et al., "The activation of protein kinase C induces higher production of reactive oxygen species by mononuclear cells in patients with multiple sclerosis than in controls," 1999, pp. 412-416, vol. 48, No. 7, Inflamm Res., Abstract only.

Wiernsperger, "Oxidative Stress as a Therapeutic Target in Diabetes: Revisitng the Controversy," 2003, pp. 579-585, vol. 29, Diabetes Metab.

Winyard et al., "Antioxidants, Redox-Regulated Transcription Factors, and Inflammation," 1997, pp. 403-421, vol. 38, Advances in Pharmacology, Abstract only.

Wolff et al., "Autoxidative glycosylation: free radicals and glycation theory," 1989, pp. 259-275, vol. 304, Prog Clin Biol Res.

Yamagishi et al., "Hyperglycemia Potentiates Collagen-Induced Platelet Activation Through Mitochondrial Superoxide Overproduction," Jun. 2001, pp. 1491-1494, vol. 50, Diabetes.

Yamagishi et al., "Leptin Induces Mitochondrial Superoxide Production and Monocyte Chemoattractant Protein-1 Expression in Aortic Endothelial Cells by Increasing Fatty Acid Oxidation via Protein Kinase A," Jul. 2001, pp. 25096-25100, vol. 276, The Journal of Biological Chemistry.

Yao et al., "Oxidative Damage and Schizophrenia," 2001, pp. 287-310, vol. 15(4), CNS Drugs.

Yao et al., "Increased Nitric Oxide Radicals in Postmortem Brain From Patients With Schizophrenia," 2004, pp. 923-934, vol. 30, No. 4, Schizophr Bull.

Yoshida et al., "Targeted Disruption of the Mouse Sod I Gene Makes the Hearts Vulnerable to Ischemic Reperfusion Injury," 2000, pp. 264-269, vol. 86, Circulation Research.

Zandi et al., "Reduced Risk of Alzheimer Disease in Users of Antioxidant Vitamin Supplements," 2004, pp. 82-88, vol. 61, Arch. Neurol.

Zubenko et al., "A cell membrane correlate of tardive dyskinesia in patients treated with phenothiazines," 1986, pp. 230-236, vol. 88, No. 2, Abstract Only, Psychopharmacology.

* cited by examiner

USE OF COLLISMYCIN AND DERIVATIVES THEREOF AS OXIDATIVE STRESS INHIBITORS

CROSS-REFERENCE TO RELATED APPLICATIONS

This application is filed under the provisions of 35 USC §371 based on International Application No. PCT/EP06/07521 filed Jul. 28, 2006, which in turn claims the priority of European Patent Application No. 05380175.9 filed Jul. 29, 2005. The disclosures of such international application and European patent application are hereby incorporated herein by reference in their respective entireties, for all purposes.

FIELD OF THE INVENTION

The present invention relates to the use of Collismycin and derivatives thereof as inhibitors of oxidative stress in cells and their use for the preparation of medicaments for the treatment and/or prevention of oxidative stress-induced diseases or conditions, especially neurodegenerative diseases, such as Alzheimer's Disease and Parkinson's Disease.

BACKGROUND OF THE INVENTION

Alzheimer's disease (AD) and Parkinson's disease (PD) are the most frequent progressive neurodegenerative diseases affecting millions of people in the world. Because a significant percentage of patients share common clinical and pathological features from both entities, this seems to indicate the existence of a common pathological mechanism. Based on in vitro and in situ data, an unified molecular oxidative stress model induced by dopamine (DA), 6-hydroxydopamine (6-OHDA); 5,6 & 5,7-dihydrytryptamine (5,6 & 5,7 MT); amyloid beta 25-35 (Aβ25-35), and metals [e.g. iron ($Fe^{2+}$), copper ($Cu^{2+}$), zinc ($Zn^{2+}$), manganese ($Mn^{2+}$)] has been widely proposed as a possible explanation of neural loss in AD/PD overlapping cases. This hypothesis might contribute to a better understanding of the pathophysiology cascades of both disorders, and also support the notion that oxidative stress generated by $H_2O_2$ represent an essential molecule of intracellular signalization leading to cell death.

Therefore, an interesting approach for developing new pharmaceutical compounds for treating neurodegenerative diseases may be designing compounds which inhibit cellular oxidative stress. Reactive oxygen species (ROS), such as oxygen radical superoxide ($O_2$) or hydrogen peroxide ($H_2O_2$), are produced during normal metabolic processes and perform several useful functions (Reactive oxygen species and the central nervous system, Halliwell B., J Neurochem.; 1992, 59 859: 1609-1623). Cells are provided with several mechanisms to control levels of these oxidative agents, for instance, superoxide dismutase (SOD), glutathione or vitamin E. In normal physiological conditions, a balance between ROS and these anti-oxidative mechanisms exists. An excessive production of ROS and a loss of efficiency of the anti-oxidative defences can lead to pathological conditions in cells and provoke tissue damage. This event seems to occur more dramatically in neurons, because of their high rate of metabolic activity, and thus seems to be related to a series of degenerative processes, diseases and syndromes, for example, Alzheimer's Disease, Parkinson's Disease, amyotrophic lateral sclerosis (ALS) and schizophrenia (Glutathione, oxidative stress and neurodegeneration, Schulz et al., Eur. J. Biochem.; 2000, 267. 4904-4911). Also other diseases or pathological conditions have been related to oxidative stress, such as Huntington's Disease (Oxidative damage in Himtington's disease, Segovia J. and Perez-Severiano F, Methods Mol. Biol; 2004; 207: 321-334), brain injuries, such as stroke and ischemia, (Oxidative Stress in the Context of Acute Cerebrovascular Stroke, El Kossi et al., Stroke; 2000; 31: 1889-1892), diabetes (Oxidative stress as a therapeutic target in diabetes: revisiting the controversy, Wiernsperger N F, Diabetes Metab.; 2003; 29, 579-85), multiple sclerosis (The role of oxidative stress in the pathogenesis of multiple sclerosis: the need for effective antioxidant therapy, Gilgun-Sherki Y. et al., J. Neurol: 2004; 251 (3): 261-8), epilepsy (Oxidative injury in epilepsy: potential for antioxidant therapy?, Costello D. J. and Delanty N., Expert. Rev. Neurother.; 2004; 4(3): 541-553), atherosclerosis (The oxidative stress hypothesis of atherogenesis, Iuliano L., Lipids; 2001; 36 suppl: S41-44), Friedreich's Ataxia (Oxidative stress mitochondrial dysfuntion and cellular stress response in Friedreich's ataxia, Calabrese et al., J. Neurol. Sci.; 2005) and heart failure (Oxygen, oxidative stress, hypoxia and heart failure, Giordano F. J., J. Clinic. Invest.; 2005; 115 (3): 500-508). Treatments that lead to an enhancement of the anti-oxidative mechanisms may slow the progression of some of the mentioned diseases.

Collismycins are 2,2'-bypiridine molecules which have been isolated from *Streptomyces* species. Several kinds of these molecules were firstly isolated by Gomi et al. (Novel Antibiotics SF2738A, B and C and their analogues produced by *Streptomyces* sp., Gomi et al., J. Antibiot., 1994, 47:1385-1394) from a culture of *Streptomyces* sp. SF2738, and their structure was described by spectral analyses and chemical conversion. Biological activities of different types of collismycins were also studied and, among them, specially Collismycin A was described to be endowed with antibiotic activity against some bacteria and a wide range of fungi. This antifungal activity against some species, such as, *Saccharomyces cerevisiae* and *Candida albicans*, has been demonstrated by Stadler et al. (Antifungal Actinomycete Metabolites Discovered in a Differential Cell-Based Screening Using a Recombinant TOPO1 Deletion Mutant Strain, Stadler et al., Arch. Pharm. Med. Chem., 2001, 334: 143-147). Two yeast strains, a wild type (ScAL 141) and a recombinant topoisomerase 1 (TOPO1) deletion mutant (ScAL 143), were used for the screening of compounds produced by actinomycetes strains WS 1410 and BS 1465. They were also used to test the biological activities of collismycins, among other compounds, with the activity of camptothecin as a reference. Results show that the mechanism of action of collismycins is not based on the inhibition of topoisomerase 1, because collismycins are active against both wild type and mutant yeast strains.

Cytotoxicity is another biological activity that has been described for some collismycins. This property was also demonstrated by Gomi et al. (see above) in a study of the cytotoxic ability of these molecules on P388 murine leukaemia cells. In JP5078322 Collismycin is related to the use of Collismycins A and B as antitumoral substances, useful as carcinostatic agents, for parenteral or oral administration. A lot of other patent publications refer to the use of Collismycins A and B in combination with other antitumoral agents. This is the case, for example, of WO02/053138, which discloses the use of incensole and/or furanogermacrens, derivatives, metabolites and precursors thereof in the treatment of neoplasia, particularly resistant neoplasia and immune dysregulatory disorders. These compounds may be administered alone or in combination with conventional chemotherapeutic, anti-viral, anti-parasite agents, radiation and/or surgery. The listed chemotherapeutic agents include Collismycins A and B.

Another biological activity of collismycins was described by Shindo et al. in 1994 (Collismycins A and B. novel non-steroidal inhibitors of dexamethasone-glucocorticoid receptor binding, Shindo et al., J. Antibiot., 1994, 47: 1072-1074). It was suggested that Collismycin A and its isomer B could have an anti-inflammatory activity inhibiting the dexamethasone-glucocorticoid receptor binding, although no complementary results to this study seem to have been published.

A synthesis of Collismycin A has been described by Trecourt et al. in 1998 (First Synthesis of Cacrulomycin E and Collismycins A and C. A New Synthesis of Caerulomycin A, Trecourt et al. J. Org. Chem., 1998, 63:2892-2897) starting from 2,2-bipyridine N-oxide. Functionalization at C-4 and C-6 through different pathways leads to 6-bromo-4-methoxy-2,2'-bipyridines; a subsequent metalation reaction introduces a methylthio moiety at C-5. In a last step of the synthesis pathway, Br at C-6 is substituted by a formyl group which reacts with hydroxylamine to provide Collismycin A. This document is herewith incorporated by reference into the present application.

In particular, Collismycin A presents the following structure:

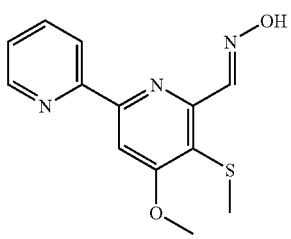

and Collismycin B:

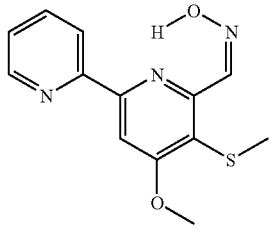

Some other 2,2'-bipyridine compounds with structures close to that of Collismycin have been described in the literature.

Some examples are: Pyrisulfoxin-A (N. Tsuge et al., J. Antibiot. 52 (1999) 505-7)

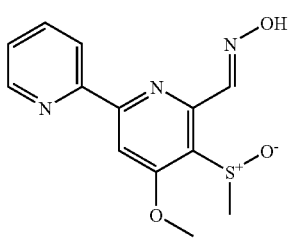

Caerulomycin-B; Cerulomycin-B

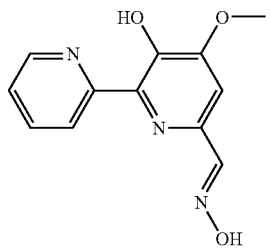

Caerulomycin-C; Cerulomycin-C

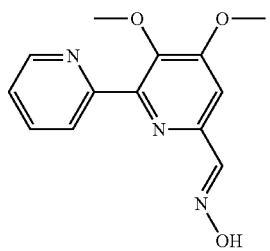

Caerulomycin; Caerulomycin-A; Cerulomycin

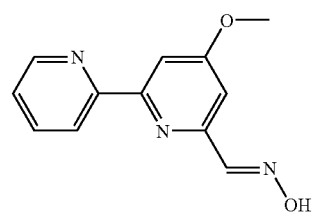

SUMMARY OF THE INVENTION

It has now been found that Collismycin A and close synthetic derivatives thereof exhibit a strong oxidative stress inhibition in cells.

Accordingly, the present invention is related to the use of a compound of formula (I)

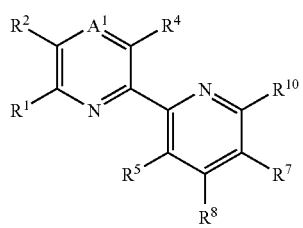

or a pharmaceutically acceptable salt, prodrug or solvate thereof, wherein
$A^1$ is selected from —C($R^3$)— and —N—,
$R^1$, $R^2$, $R^3$, $R^4$, and $R^5$ are independently selected from hydrogen, substituted or unsubstituted alkyl, —CN, —O—$R^a$, —N$R^b R^c$, —NO$_2$, or halogen;
$R^7$ is selected from halogen, preferably fluor, hydrogen and —S—$R^9$;

$R^{10}$ is selected from —CN, —CH=N—O—$R^6$, and —CH$_2$—O—$R^6$,
$R^8$ is selected from hydrogen, —O—$R^{11}$, and —S—$R^9$,
with the proviso that at least one of $R^7$ and $R^8$ is different from hydrogen,
$R^6$ and $R^{11}$ are independently selected from hydrogen, substituted or unsubstituted alkyl, —NR$^b$R$^c$, —C(=O)R$^d$;
$R^9$ is selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aralkyl, substituted or unsubstituted aryloxy, halogen;
$R^a$, $R^b$, $R^c$ and $R^d$ are each independently selected from hydrogen, substituted or unsubstituted alkyl, substituted or unsubstituted cycloalkyl, substituted or unsubstituted alkenyl, substituted or unsubstituted aryl, substituted or unsubstituted aralkyl, substituted or unsubstituted heterocyclyl, or halogen; in the preparation of a medicament for the treatment and/or prevention of a oxidative-stress-induced disease or condition selected from the group formed by Alzheimer's Disease, Parkinson's Disease, Huntington's Disease, Amyotrophic Lateral Sclerosis (ALS), Multiple Sclerosis (ML), Friedreich's ataxia, tardive dyskynesia, brain injuries, such as ischemia, reperfusion injury or stroke, myocardial infarction, schizophrenia, atherosclerosis, heart failure, diabetes, specially diabetes type II, epilepsy and AIDS dementia.

According to a preferred embodiment, $R_1$, $R_2$, $R_3$, $R_4$ and $R_5$ are independently selected from hydrogen, substituted or unsubstituted alkyl or halogen.

In another embodiment $R_7$ is preferably —S—$R_9$.

In a further preferred embodiment $R^7$ is —S—$R^9$, $R^{10}$ is —CH=N—O—$R^6$, $R^8$ is —O—$R^{11}$, wherein $R^6$, $R^9$ and $R^{11}$ are independently selected from hydrogen and substituted or unsubstituted alkyl.

More preferably, in the compound of formula (I) $R_7$ is —S—$R^9$, $R^{10}$ is —CH=N—O—$R^6$, $R^8$ is -O-$R^{11}$ and $R^1$, $R^2$, $R^3$, $R^4$, $R^5$, $R^6$, $R^9$ and $R^{11}$ are independently selected from hydrogen and unsubstituted alkyl.

Even more preferably, $R^7$ is —S—$R^9$, $R^1$, $R^2$, $R^3$, $R^4$ and $R^5$ are hydrogen; $R^8$ is -0-$R^{11}$, $R^{10}$ is —CH=N—OH; wherein $R^9$ and $R^{11}$ are independently selected from unsubstituted alkyl.

In a preferred embodiment, the compound of formula (I) is

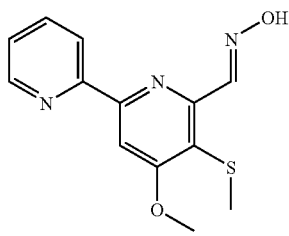

or its pharmaceutically acceptable salts and solvates.

The term "oxidative stress-induced disease or condition", as used herein, means any disease or other deleterious condition induced or co-induced by oxidative stress.

Preferably, the oxidative stress-induced disease or condition is a neurodegenerative disease or condition.

According to a preferred embodiment of the present invention, the neurodegenerative disease is Alzheimer's Disease.

According to another preferred embodiment, the neurodegenerative disease or condition is Parkinson's Disease.

According to an additional embodiment, the oxidative stress-induced disease or condition is stroke or ischemia.

Another aspect of this invention relates to a method of treating and/or preventing an oxidative stress-induced disease or condition selected from the group formed by Alzheimer's Disease, Parkinson's Disease, Huntington's Disease, Amyotrophic Lateral Sclerosis (ALS), Multiple Sclerosis (ML), Friedreich's ataxia, tardive dyskynesia, brain injuries, such as ischemia, reperfusion injury or stroke, myocardial infarction, schizophrenia, atherosclerosis, heart failure, diabetes, specially diabetes type II, epilepsy and AIDS dementia, with a compound as described above, which method comprises administering to a patient in need of such a treatment a therapeutically effective amount of a compound of formula (I) as defined in the claims or a pharmaceutically acceptable salt, prodrug or solvate thereof, or a pharmaceutical composition thereof.

DETAILED DESCRIPTION OF THE INVENTION

Figure 1:
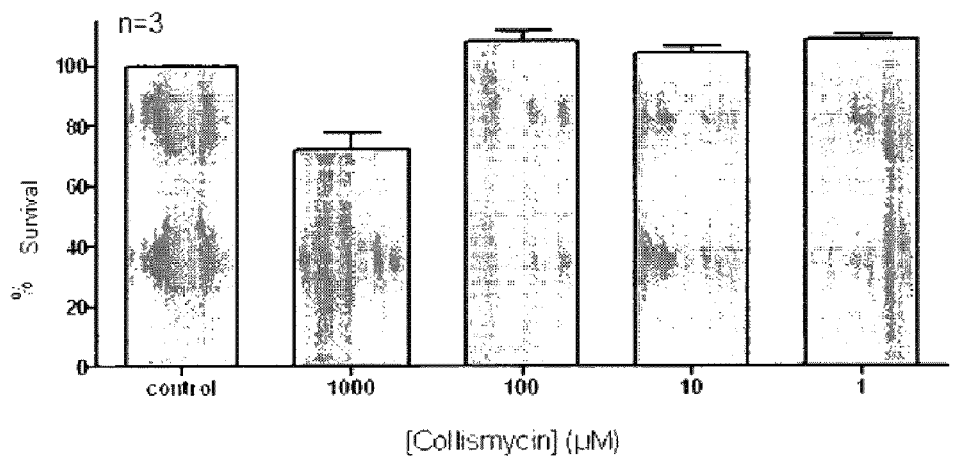
FIG. 1.—Results of toxicity assay in SHSY5Y human neuroblastoma cells, Lactate dehydrogenase activity is measured after incubation at different Collismycin A concentrations.

The typical compounds of this invention show good properties regarding inhibition of oxidative stress caused by $H_2O_2$ and cellular protection against the deleterious effects of the toxine 6-hydroxidopamine, which are similar or even better than the properties of the widely used control NAC(N-Acetylcysteine); simultaneously, the compounds show very high levels of cell survival.

In the above definition of compounds of formula (I) the following terms have the meaning indicated:

"Alkyl" refers to a straight or branched hydrocarbon chain radical consisting of carbon and hydrogen atoms, containing no saturation, having one to eight carbon atoms, and which is attached to the rest of the molecule by a single bond, e. g., methyl, ethyl, n-propyl, i-propyl, n-butyl, t-butyl, n-pentyl, etc. Alkyl radicals may be optionally substituted by one or more substituents such as halo, hydroxy, alkoxy, carboxy, cyano, carbonyl, acyl, alkoxycarbonyl, amino, nitro, mercapto and alkylthio. "Aryl" refers to a phenyl, naphthyl, indenyl, fenanthryl or anthracyl radical, preferably phenyl or naphthyl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl and alkoxycarbonyl, as defined herein.

"Aralkyl" refers to an aryl group linked to an alkyl group. Preferred examples include benzyl and phenethyl.

"Cycloalkyl" refers to a stable 3- to 10-membered monocyclic or bicyclic radical which is saturated or partially saturated, and which consist solely of carbon and hydrogen atoms. Unless otherwise stated specifically in the specification, the term "cycloalkyl" is meant to include cycloalkyl radicals which are optionally substituted by one or more such as alkyl, halo, hydroxy, amino, cyano, nitro, alkoxy, carboxy and alkoxycarbonyl.

"Halo" refers to bromo, chloro, iodo or fluoro.

"Heterocycle" refers to a heterocyclyl radical. The heterocycle refers to a stable 3- to 15 membered ring which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran.

References herein to substituted groups in the compounds of the present invention refer to the specified moiety that may be substituted at one or more available positions by one or more suitable groups, e.g., halogen such as fluoro, chloro, bromo and iodo; cyano; hydroxyl; nitro; azido; alkanoyl such as a C1-6 alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl or naphthyl and aralkyl such as benzyl. Unless otherwise indicated, an optionally substituted group may have a substituent at each substitutable position of the group, and each substitution is independent of the other.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon or $^{15}$N-enriched nitrogen are within the scope of this invention.

The term "pharmaceutically acceptable salts, solvates, prodrugs" refers to any pharmaceutically acceptable salt, ester, solvate, or any other compound which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

For instance, pharmaceutically acceptable salts of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium, ammonium, magnesium, aluminium and lithium salts, and organic alkali salts such as, for example, ethylenediamine, ethanolamine, N,N-dialkylenethanolamine, triethanolamine, glucamine and basic aminoacids salts.

Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species Any compound that is a prodrug of a compound of formula (I) is within the scope of the invention. The term "prodrug" is used in its broadest sense and encompasses those denvatives that are converted in vivo to the compounds of the invention Such derivatives would readily occur to those skilled in the art, and include, depending on the functional groups present in the molecule and without limitation, the following derivatives of the present compounds' esters, amino acid esters, phosphate esters, metal salts sulfonate esters, carbamates, and amides. Examples of well known methods of producing a prodrug of a given acting compound are known to those skilled in the art and can be found e.g in Krogsgaard-Larsen et al. "Textbook of Drug Design and Discovery" Taylor & Francis (April 2002).

The compounds of formula (I) defined above can be obtained from natural sources, by synthetic modifications of the natural compound or by total synthesis using available synthetic procedures. As mentioned above, according to Trecourt et al (First Synthesis of Caerulomycin E and CoUismycins A and C A New Synthesis of Caenilomycin A, Trecourt et al J Org Chem, 1998, 63: 2892-2897), a synthesis of Collismycin A starting from 2-2'-bipyπdine-N-oxide can be undertaken. This document is herewith incorporated by reference into the present application.

This pathway mainly involves efficiently controlled reactions such as metalation and cross-coupling:

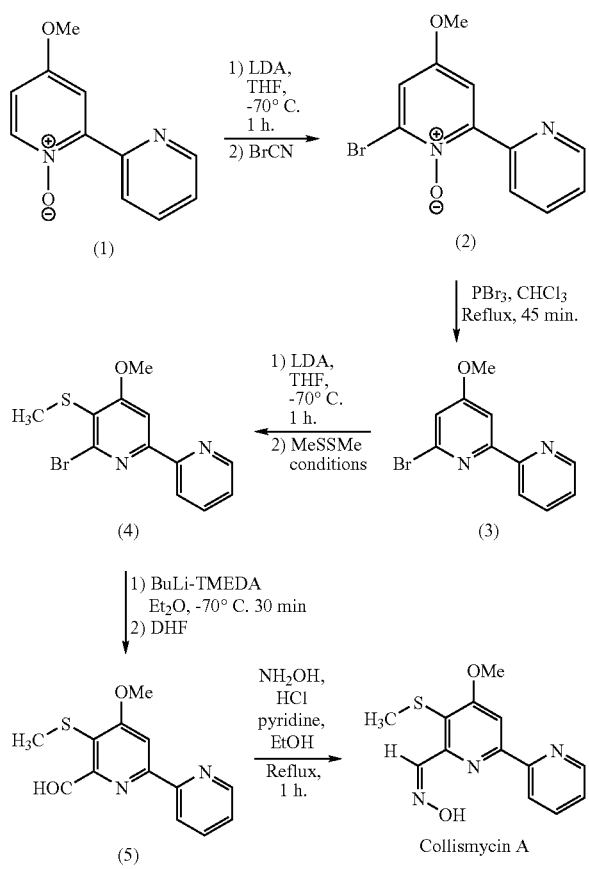

The synthesis pathway starts from 4-methoxy-2,2'-bipyridine N-oxide (1), which can be easily prepared from 2,2'-bypiridine by a known three-step sequence (Wenkert, D., Woodward, R. B., J Org Chem. 1983, 48, 283). The first part of the synthesis pathway involves functionalization at carbon in position six (C-6) of compound (1). A metalation of 4-methoxy-2,2'-bipyridine N-oxide using LDA at −70° C. and BrCN as electrophile is undertaken in order to obtain a bromine N-oxide (2). This molecule is subsequently reduced with PBr$_3$, rendering a good yield and leading to 6-bromo-4-methoxy-2,2'-bipyridine (3).

In a second sequence of reactions, the obtained bromine-bipyridine is subjected to another metalation with the same conditions of LDA at −70° C. but using methyl disulfide as electrophile (Turner J. A., J. Org. Chem. 1983, 48, 3401) to introduce a methyltio moiety at C-5, thus obtaining compound (4). Conditions have to be carefully optimised to avoid side replacement of the brome at C-6 by a methyltio moiety before hydrolysis (First Synthesis of Caerulomycin E and Collismycins A and C. A New Synthesis of Caenilomycin A, Trecourt et al. J. Org. Chem., 1998, 63:2892-2897). To reach the target molecule, Collismycin A, the functionalization of C-6 is carried out through a strategy of bromine-lithium exchange. The chelate BuLi-TMEDA performs this exchange, and the obtained lithium derivative is then quenched in presence of DMF to give an aldehyde (5). Reacting this aldehyde with hydroxylamine leads to Collismycin A (6).

Other alternative procedures may be found in Org. Lett. 2002, 4(14) 2385-2388; J. Org. Chem. 2002, 67(10), 3272-3276; J. Org. Chem. 1996, 61(5), 1673-1676.

Additional alternative procedures will be apparent to the person skilled in the art, using standard reactions in organic Chemistry such as those described in "March's Advanced Organic Chemistry" 5$^{th}$ Edition, 2001 Wiley-Interscience.

The compounds of the invention may be in crystalline form either as free compounds or as solvates (e.g. hydrates) and it is intended that both forms are within the scope of the present invention. Methods of solvation are generally known within the art. Suitable solvates are pharmaceutically acceptable solvates. In a particular embodiment the solvate is a hydrate.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

The compounds of the present invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

The compounds and compositions of this invention may be used with other drugs to provide a combination therapy. The other drugs may form part of the same composition, or be provided as a separate composition for administration at the same time or at different time.

The following examples are intended to further illustrate the invention. They should not be interpreted as a limitation of the scope of the invention as defined in the claims.

EXAMPLES

Synthesis

Compounds of formula (I) were prepared based on the synthesis pathway detailed above. Detailed synthesis of some of the compounds is hereinafter included:

Example 1

Preparation of Compound I

4-Methylsulfanyl-[2,2']bipyridinyl-6-carbonitrile

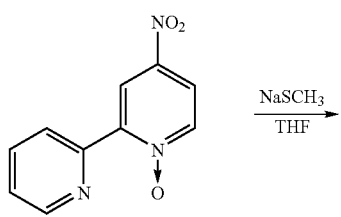

4-Nitro-[2,2']bipyridinyl 1-oxide

-continued

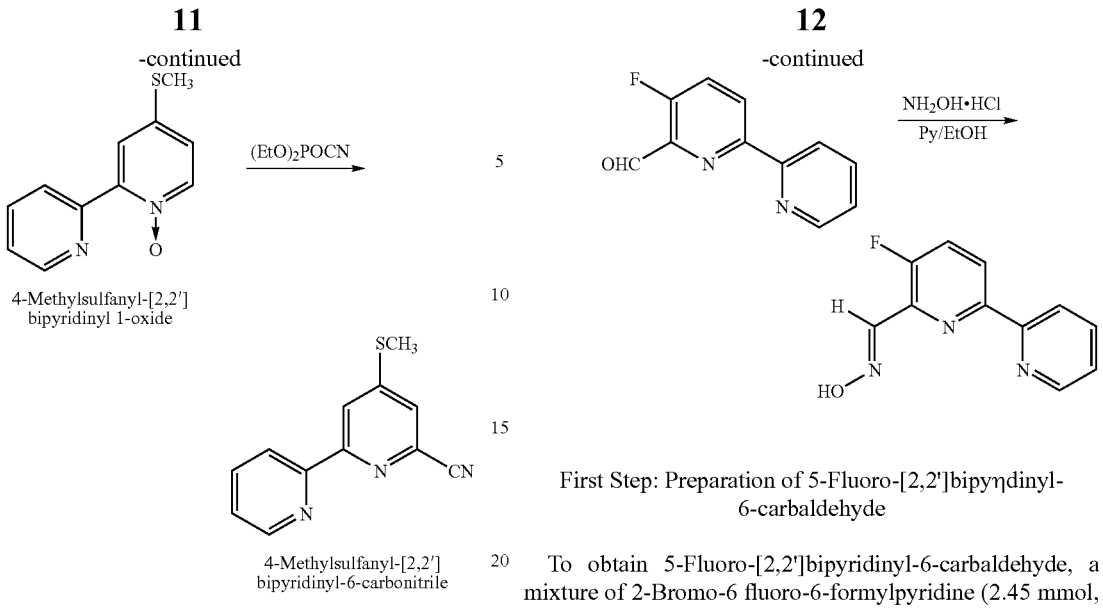

4-Methylsulfanyl-[2,2']bipyridinyl 1-oxide

4-Methylsulfanyl-[2,2']bipyridinyl-6-carbonitrile

4-Methylsulfanyl-[2,2']bipyridinyl 1-oxide

4-Nitro-[2,2']bipyridinyl 1-oxide (1.00 g, 4.6 mmol) (D. Wenkert; R. B. Woodward, J. Org. Chem. 1983, 48, 283-289) and sodium methylthiolate (0.73 g, 10.3 mmol) were refluxed in tetrahydrofuran (30 mL) for 6 hours. The mixture was allowed to reach room temperature and the solvent was evaporated in vacuo. The oily residue obtained was redissolved in methylene chloride and washed sequentally with water and a saturated solution of sodium chloride, dried with anhydrous sodium sulfate and evaporated. Pure 4-methylsulfanyl-[2,2']bipyridinyl 1-oxide was isolated after flash chromatography (SiO$_2$, MeOHZCH$_2$Cl$_2$ 1:25) as a yellowish oil that slowly solidified (0.59 g, 59% yield).

$^1$H NMR (400 MHz, CDCl$_3$):
8.91, 8.68, 8.14, 7.95, 7.80, 7.32, 7.05, 2.53
$^{13}$C NMR (100 MHz, CDCl$_3$):
149.27, 149.23, 146.41, 139.92, 139.15, 136.21, 125.65, 124.34, 123.30, 121.80, 14.82

Second Step: Preparation of 4-Methylsulfanyl-[2,2'] bipyridinyl-6-carbonitrile 4-Methylsulfanyl-[2,2']bipyridinyl 1-oxide (480 mg, 2.20 mmol) was treated under nitrogen with diethyl phosphorocyanidate and triethylamine in dry acetonitrile following a described procedure (I. Antonioni; G. Cristalli; P. Franchetti; M. Grifantini; S. Martelli, Il Farmaco, 1986, 41, 346-354). Crystallization in ethyl acetate afforded 4-methylsulfanyl-[2, 2']bipyridinyl-6-carbonitrile as a white solid (360 mg, 72% yield)

$^1$H NMR (400 MHz, CDCl$_3$):
8.67, 8.47, 8.44, 8.00, 7.85, 7.46, 7.37, 2.61
$^{13}$C NMR (100 MHz, CDCl$_3$):
156.72, 153.83, 153.59, 149.17, 137.20, 132.88, 124.79, 124.08, 121.82, 119.38, 117.30, 13.96

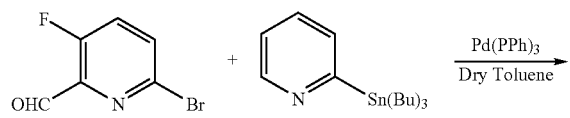

First Step: Preparation of 5-Fluoro-[2,2']bipyridinyl-6-carbaldehyde

To obtain 5-Fluoro-[2,2']bipyridinyl-6-carbaldehyde, a mixture of 2-Bromo-6 fluoro-6-formylpyridine (2.45 mmol, 0.5 g) and 2-tributylstannyl-pyridine (2.94 mmol; 1.08 g) and Tetrakis(triphenylphosphine)-palladium(0) (0.09 mmol, 0.103 g) in anhydrous toluene was refluxed under nitrogen for 54 h. The resulting brown mixture was evaporated in vacuo and the dark, muddy liquid was dissolved in dichloromethane. The organic phase was washed with aqueous HCl 6M (3×). To remove the product from the solution the combined aqueous layers were transferred dropwise in aqueous ammonia (10%) under cooling. The resulting oil was extracted with dichloromethane (3×). The organic phases were washed with ammonia and water, and the solvent was removed. The resulting crude was purified by column chromatography using as eluent Acetate/Hexane, 1/2, thus obtaining 5-Fluoro-[2,2']bipyηdinyl-6-carbcddehyde (Ulrich, S. Schubert; Christian Eschbaumer; Marcel Heller. Org. Lett, 2000, 2(21), 3373-3376).

Yield: 200 mg (43%), yellow solid.
$^1$H-NMR (CDCl$_3$): 10.2 (s, 1H); 8.64 (m, 2H); 8.45 (d, 1H, J=7.9 Hz); 7.81 (t, 1H, J=7.6 Hz); 7.63 (t, 1H, J=9.2 Hz); 7.33 (m, 1H)
$^{13}$C-NMR (CDCl$_3$): 189.8 (CHO, J=3.3 Hz); 159.0 (C—F, J=275.5 Hz); 153.8 (py); 152.7 (J=4.5 Hz); 149.1 (py); 139.2 (J=1.5 Hz); 137.0 (py); 127.0 (0.7=4.5 Hz); 126.2 (J=18.8 Hz); 124.2 (py); 121.0 (py).

Second Step: Preparation of 5-Fluoro-[2,2']bipyridinyl-6-carbaldehyde oxime

5-Fluoro-[2,2']bipyridinyl-6-carbaldehyde (0.36 mmol, 73 mg), hydroxylamine hydrochloride (1.8 mmol, 125 mg), pyridine (1.6 mmol, 0.12 mL) and EtOH were heated at reflux during 2 h. The solvent was evaporated under vacuum, and H$_2$O was added. The filtration of the white precipitate obtained provided the final product without needing any purification (Florence Mongin; Francois Trecourt; Bruno Gervais; Oliver Mongin; Guy Quequiner, J. Org. Chem., 2002, 67, 3272-3276). Yield: 47 mg (60%), white solid. $^1$H-NMR (DMSO): 12.0 (N—OH); 8.76 (d, 1H, J=4.4 Hz); 8.46 (dd, 1H, J$_1$=8.5 Hz, J$_1$=3.4 Hz); 8.40 (d, 1H, J=7.9 Hz); 8.34 (s, 1H); 8.01 (m, 2H); 7.54 (m, 1H)
$^{13}$C-NMR (DMSO): 157.5 (C—F, J=270.5 Hz); 153.8 (py); 151.3 (J=4.5 Hz); 149.2 (py); 145.2 (C═N, J=6.2 Hz); 138.9 (J=1.5 Hz); 137.4 (py); 125.5 (J=18.5 Hz); 124.2 (py); 122.1 (J=5.2 Hz); 120.4 (py).

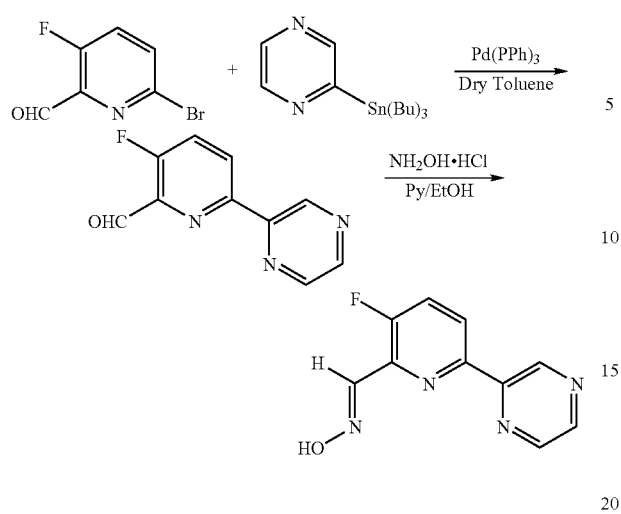

First Step: Preparation of 3-Fluoro-6-pyrazin-2-yl-pyridine-2-carbaldehyde

To obtain 3-Fluoro-6-pyrazin-2-yl-pyridine-2-carbaldehyde, a mixture of 2-Bromo-6 fluoro-6-formylpyridine (2.45 mmol, 0.5 g) and 2-tributylstannyl-pyridine or 2-tributylstannyl-pyrazine (2.94 mmol; 1.00 g) and Tetrakis(triphenylphosphine)-palladium(0) (0.09 mmol, 0.103 g) in anhydrous toluene was refluxed under nitrogen for 54 h. The resulting brown mixture was evaporated in vacuo and the dark, muddy liquid was dissolved in dichloromethane. The organic phase was washed with aqueous HCl 6M (3×). To remove the product from the solution the combined aqueous layers were transferred dropwise in aqueous ammonia (10%) under cooling. The resulting oil was extracted with dichloromethane (3×). The organic phases were washed with ammonia and water, and the solvent was removed. The resulting crude was purified by column chromatography using as eluent Acetate/Hexane, 1/1, to obtain 3-Fluoro-6-pyrazin-2-yl-pyridine-2-carbaldehyde (Ulrich, S. Schubert; Christian Eschbaumer; Marcel Heller. Org. Lett, 2000, 2(21), 3373-3376). Yield: 68 mg (10%), white solid. $^1$H-NMR (CDCl$_3$): 10.25 (s, 1H); 9.69 (d, 1H, J=1.5 Hz); 8.64 (m, 3H); 7.7 (t, 1H, J=8.95 Hz) $^{13}$C-NMR (CDCl$_3$): 189.5 (CHO, J=3.3 Hz); 159.0 (C—F, J=275.5 Hz); 150.8 (J=A.6 Hz); 148.9; 145.0; 143.5; 143.2; 139.7 (J=7.6 Hz); 127.4 (J=6.4 Hz); 126.6 (J=18.8 Hz)

Second Step: Preparation of 3-Fluoro-6-pyrazin-2-yl-pyridine-2-carbaldehyde oxime To obtain 3-Fluoro-6-pyrazin-2-yl-pyridine-2-carbaldehyde oxime, 3-Fluoro-6-pyrazin-2-yl-pyridine-2-carbaldehyde (0.24 mmol, 48 mg), hydroxylamine hydrochloride (1.18 mmol, 82.2 mg), pyridine (1.01 mmol, 0.082 mL) and EtOH were heated at reflux for 2 h. The solvent was evaporated under vacuum, and H$_2$O was added. The filtration of the white precipitate obtained provided the final product without needing any purification (Florence Mongin; Francois Trecourt; Bruno Gervais; Oliver Mongin; Guy Quequiner, J. Org. Chem., 2002, 67, 3272-3276).

Yield: 30 mg (58%), white solid.

$^1$H-NMR (DMSO): 12.0 (N—OH); 9.49 (d, 1H, J=1.4 Hz); 8.75 (m, 2H); 8.35 (dd, 1H, J$_1$=8.8 Hz, J$_2$=3.8 Hz); 8.31 (s, 1H); 7.99 (m, 1H).

$^{13}$C-NMR (DMSO): 157.5 (C—F, J=270.5 Hz); 149.5 (J=4.5 Hz); 148.9; 145.2 (C═N, J=6.2 Hz); 144.9; 143.9; 142.2; 139.4 (J=7.5 Hz); 125.9 (J=18.5 Hz); 122.7 (J=5.2 Hz)

Biology

The following compounds were assayed to determine their toxicity, their capacity of protecting against hydrogen peroxide-induced cell death and their capacity of protecting against 6-OHDA-induced cell death.

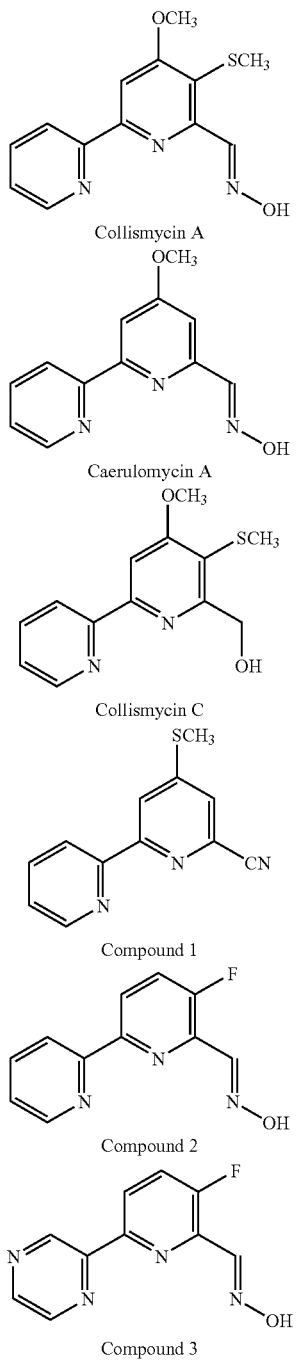

Toxicity

The potential effects on cell viability of the assayed compounds are assayed in SH-SY5Y human neuroblastoma cells, by quantification of Lactate dehydrogenase (LDH) activity release. SH-SY5Y human neuroblastoma cells are seeded into 96-well culture plates at 104 cells/well. The medium is then removed and the cells incubated with different concentrations of the compounds during 24 h. The compounds are tested at final concentrations of 1, 10, 100 and 1000 µM, in fresh culture medium. After 24 h, the medium is removed and cells attached to the bottom of the well are lysed by adding 50 µl of Krebs-Hepes; Triton X-100 1% during 5 minutes at room temperature. For LDH release quantification, we use the Roche cytotoxicity detection kit (Cat. No. 1 1 644 793 001). The LDH activity is measured by its absorbance at 492 nm with reference wavelength 620 nm. The results for Collismycin A are shown in FIG. 1. An effect on cell viability was only observed at 1000 µM, the highest concentration tested.

Caerulomycin A, Collismycin C and Compound 2 were assayed at a maximum concentration of 1000 µM, and resulted non toxic. Compound 1 and Compound 3 were assayed at a maximum concentration of 5 and 10 µM respectively, and resulted also non toxic.

Protection Against Hydrogen Peroxide-Induced Cell Death

The aim of this assay is to determine the neuroprotective effect of the compounds of formula (I), when human neuroblastoma cells are exposed to oxidative stress induced by hydrogen peroxide, which is highly deleterious to the cell and its accumulation causes oxidation of cellular targets such as DNA, proteins, and lipids leading to mutagenesis and cell death.

SH-SY5Y human neuroblastoma cells are seeded into 96-well culture plate at a density of 104 cells/well. Cells are exposed to the different concentrations of the compound one hour before the treatment with $H_2O_2$ 100 µM during 24 h. 5 mM NAC, a known anti-oxidant agent was used as a positive control, and preincubated 1 hour before the treatment with $H_2O_2$. After 24 h, the medium is removed and cells attached to the bottom of the well are lysed by adding 50 µl of Triton X-100 1% in Krebs-Hepes during 5 minutes at room temperature. For LDH release quantification, Roche cytotoxicity detection kit (Cat. No. 1 1 644 793 001) is used.

Figure 2:
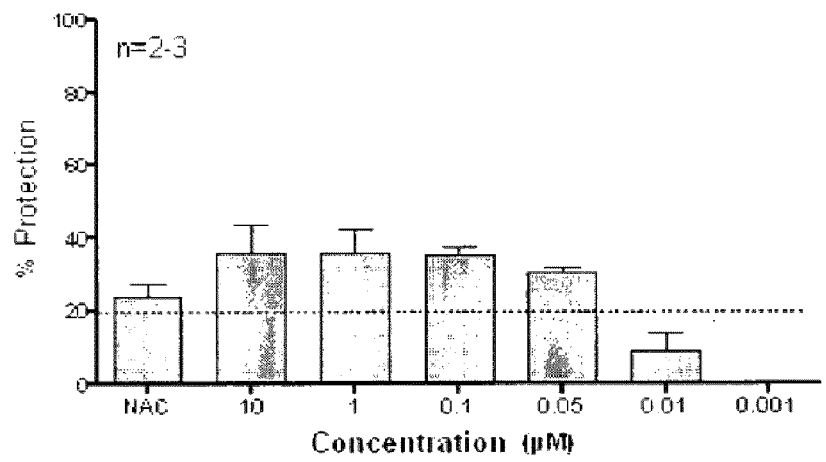
FIG. 2.—Results of neuroprotection assay on human neuroblastoma cells exposed to $H_2O_2$ induced oxidative stress, previous incubation with Collismycin A.

Results for neuroprotection of Collismycin A at different concentrations, compared to the neuroprotection of NAC 5 mM, are shown in FIG. 2.

Figure 3:
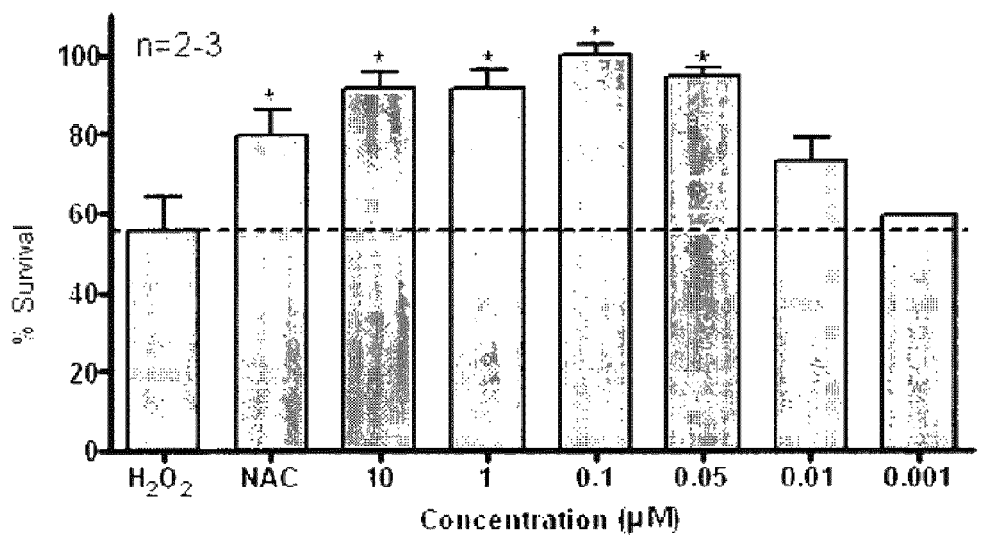
FIG. 3.—Results of cell survival assay on human neuroblastoma cells exposed to $H_2O_2$ induced oxidative stress, previous incubation with Collismycin A.

Cell survival was determined in parallel in the same assay. FIG. 3 shows the results obtained with different concentrations of Collismycin A, together with the comparative results for the control NAC at 5 mM and $H_2O_2$ alone. As can be observed from the results, Collismycin A shows a significant neuroprotective activity at 0.05 µM.

For Caerulomycin A, the lowest concentration at which neuroprotective effects were detected was 0.05 µM.

For Collismycin C and Compound 3, the lowest concentration at which neuroprotective effects were detected was 10 µM.

For Compound 1 and Compound 2, the lowest concentrations at which neuroprotective effects were detected were 5 µM and 0.5 µM, respectively.

Protection Against 6-OH DA-Induced Cell Death

The aim of this experiment is to determine the protective effect of the compounds of formula (I) against the toxicity caused by 6-hydroxydopamine (6-OHDA). This toxin induces a cell death similar to which occurs in Parkinson's disease, destroying dopaminergic neurons ("MPTP and 6-hydroxydopamine-induced neurodegeneration as models for Parkinson's disease: neuroprotective strategies"; Grunblatt E, et al.; J Neurol. 2000 April; 247 Suppl 2:1195-102). Two or three days before the experiment, the SH-SY5Y human neuroblastoma cells are seeded into 96-well culture plate at a density of $10^4$ cells/well.

Cells are exposed to the treatment with 6-OHDA and, finally, cell death is measured by LDH quantification. As positive control we used NAC. The assay is performed in two different experimental conditions:

A) NAC and the compound of formula (I) are preincubated during 2 hours before the treatment with 6-OHDA 75 µM during 16 hours. The assay is performed in medium containing 10% Foetal bovine serum.

Figure 4:
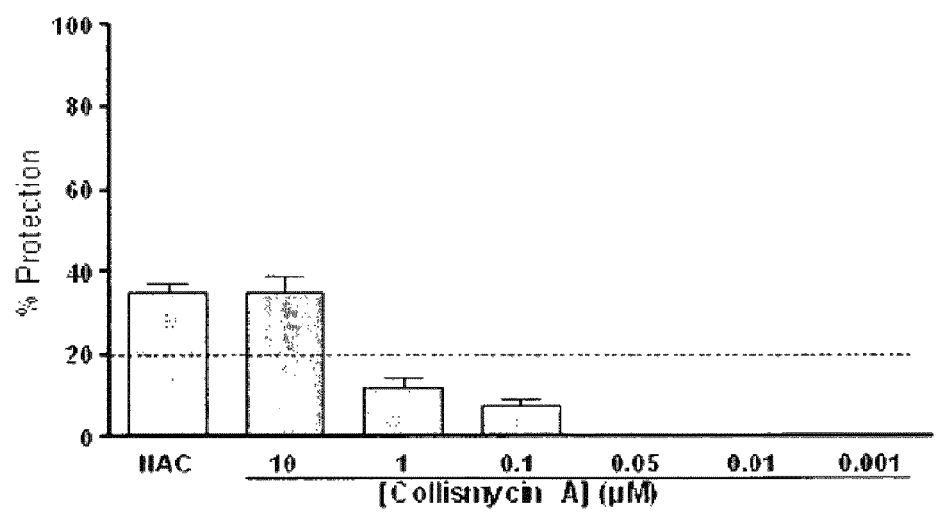
FIG. 4.—Protective effect of 2 hour preincubation with Collismycin A against toxicity caused by 6-hydroxydopamine.

The neuroprotective results against cellular death induced by 6-OHDA are shown in FIG. 4.

Figure 5:
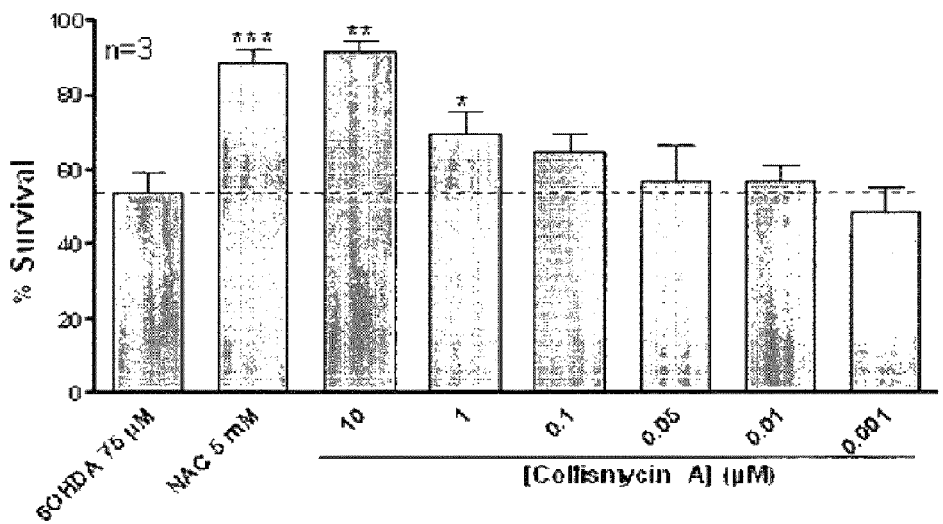
FIG. 5.—Diagram showing cell survival previous 2 hour preincubation at different concentrations of Collismycin A, compared with 6OH DA and NAC.

The results relating to cell survival in this assay, at different concentrations of Collismycin A, together with the comparative results for the control NAC at 5 mM and 6-OHDA alone, are shown in FIG. 5.

Caerulomycin A resulted neuroprotective at a minimum concentration of 1 µM. Collismycin C, Compound 2 and Compound 3 showed a neuroprotective activity at a minimum concentration of µM.

B) NAC and the compound of formula (I) are preincubated during 1 hour before the treatment with 6-OHDA 50 µM during 24 hours. The assay is performed in medium without any fetal bovine serum.

Figure 6:
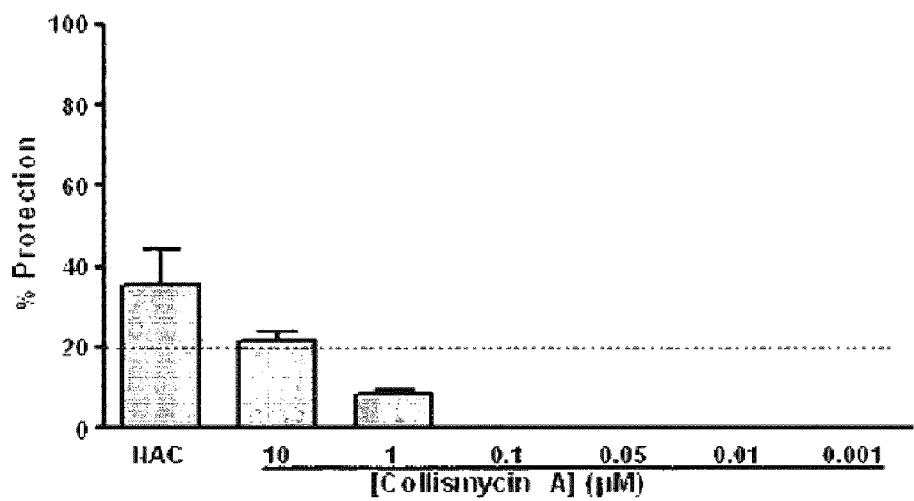
FIG. 6.—Neuroprotection against cellular death induced by 6OHDA, previous 1 hour preincubation with Collismycin A.

The neuroprotective results for Collismycin A against cellular death induced by 6-OHDA are shown in FIG. 6.

Figure 7:
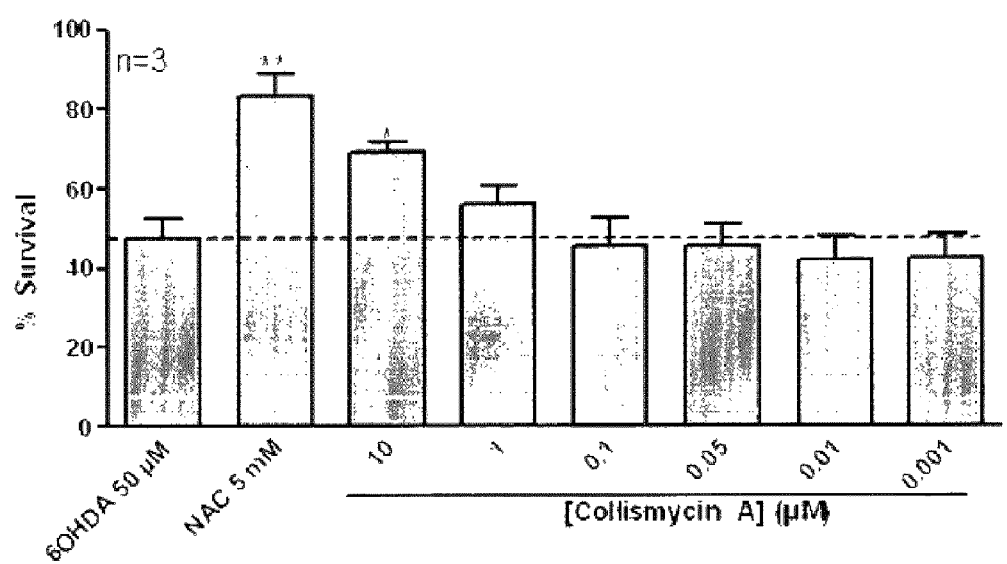
FIG. 7.—Diagram showing cell survival previous 1 hour preincubation at different concentrations of Collismycin A, compared with 6OHDA and NAC.

The results relating to cell survival in this assay, at different concentrations of Collismycin A, together with the comparative results for the control NAC at 5 mM and 6-OHDA alone, are shown in FIG. 7.

Caerulomycin A showed a neuroprotective effect at a minimum concentration of 1 µM, Collismycin C at 10 µM, and Compound 2 at 0.5 µM.

The invention claimed is:

1. A method of inhibiting oxidative stress in a patient suffering from a disease or condition selected from the group consisting of Alzheimer's Disease, Parkinson's Disease, Huntington's Disease, Amyotrophic Lateral Sclerosis (ALS), Multiple Sclerosis (MS), Friedreich's ataxia, tardive dyskynesia, brain injuries, ischemia, reperfusion injury, stroke, myocardial infarction, schizophrenia, atherosclerosis, heart failure, diabetes, diabetes type II, epilepsy and AIDS dementia, comprising administering to the subject suffering said disease or condition an effective amount of collismycin A or a pharmaceutically acceptable salt thereof.

2. The method according to claim 1, wherein the disease or condition is Alzheimer's Disease.

3. The method according to claim 1, wherein the disease or condition is Parkinson's Disease.

4. A method of inhibiting oxidative stress in a patient suffering from a disease or condition selected from the group consisting of Alzheimer's Disease, Parkinson's Disease, Huntington's Disease, Amyotrophic Lateral Sclerosis (ALS), Multiple Sclerosis (MS), Friedreich's ataxia, tardive dyskynesia, brain injuries, ischemia, reperfusion injury, stroke, myocardial infarction, schizophrenia, atherosclerosis, heart failure, diabetes, diabetes type II, epilepsy and AIDS dementia, comprising administering to the subject suffering said disease or condition an effective amount of a compound of formula (I)

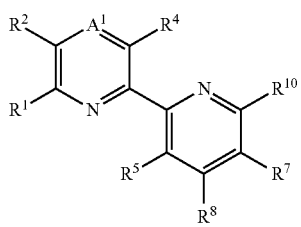

or a pharmaceutically acceptable salt thereof, wherein:
$A^1$ is selected from —C($R^3$)— and —N—;
$R^1$, $R^2$, $R^3$, $R^4$, and $R^5$ are each independently selected from hydrogen, substituted or unsubstituted alkyl, —CN, —O—$R^a$, —N$R^b R^c$, —NO$_2$, and halogen;
$R^7$ is selected from halogen, hydrogen and —S—$R^9$;
$R^{10}$ is selected from —CN, —CH=N—O—$R^6$, and —CH$_2$—O—$R^6$;
$R^8$ is selected from hydrogen, —O—$R^{11}$, and —S—$R^9$;
$R^6$ and $R^{11}$ are each independently selected from hydrogen, substituted or unsubstituted alkyl, —N$R^b R^c$, and —C(=O)$R^d$;
$R^9$ is selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aralkyl, substituted or unsubstituted aryloxy, and halogen; and
$R^a$, $R^b$, $R^c$ and $R^d$ are each independently selected from hydrogen, substituted or unsubstituted alkyl, substituted or unsubstituted cycloalkyl, substituted or unsubstituted alkenyl, substituted or unsubstituted aryl, substituted or unsubstituted aralkyl, substituted or unsubstituted heterocyclyl, and halogen;
with the proviso that at least one of $R^7$ and $R^8$ is different from hydrogen, and further wherein said compound of formula (I) is not collismycin A.

5. The method according to claim 4, wherein $R^1$, $R^2$, $R^3$, $R^4$ and $R^5$ are each independently selected from hydrogen, substituted or unsubstituted alkyl and halogen;
$R^7$ is —S—$R^9$;
$R^{10}$ is —CH=N—O—$R^6$;
$R^8$ is —O—$R^{11}$; and
$R^6$, $R^9$ and $R^{11}$ are each independently selected from hydrogen and substituted or unsubstituted alkyl.

6. The method according to claim 4, wherein:
$R^7$ is —S—$R^9$;
$R^{10}$ is —CH=N—O—$R^6$;
$R^8$ is —O—$R^{11}$; and
$R^1$, $R^2$, $R^3$, $R^4$, $R^5$, $R^6$, $R^9$ and $R^{11}$ are each independently selected from hydrogen and unsubstituted alkyl.

7. The method according to claim 5, wherein:
$R^7$ is —S—$R^9$;
$R^{10}$ is —CH=N—O—$R^6$;
$R^8$ is —O—$R^{11}$; and
$R^1$, $R^2$, $R^3$, $R^4$, $R^5$, $R^6$, $R^9$ and $R^{11}$ are each independently selected from hydrogen and unsubstituted alkyl.

8. The method according to claim 4, wherein:
$R^1$, $R^2$, $R^3$, $R^4$, $R^5$ are hydrogen;
$R^7$ is —S—$R^9$;
$R^{10}$ is —CH=N—OH;
$R^8$ is —O—$R^{11}$, and
$R^9$ and $R^{11}$ are each independently selected from unsubstituted alkyl.

9. The method according to claim 4, wherein the compound of formula (I) is selected from the group consisting of:

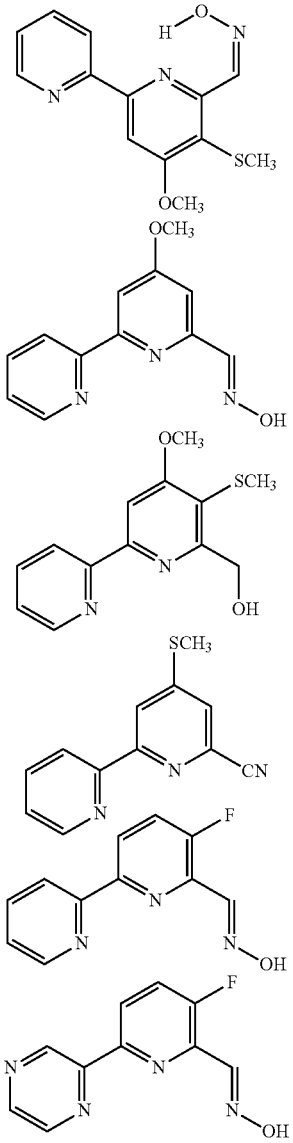

or a pharmaceutically acceptable salt thereof.

10. The method according to claim 4, wherein the compound of formula (I) is

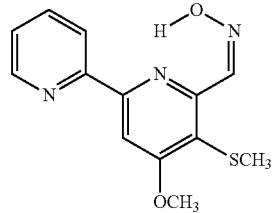

or a pharmaceutically acceptable salt thereof.

11. The method according to claim 4, wherein the disease or condition is Alzheimer's Disease.

12. The method according to claim 4, wherein the disease or condition is Parkinson's Disease.

* * * * *